US00PP14899P2

(12) United States Plant Patent

Moes

(10) Patent No.: US PP14,899 P2
(45) Date of Patent: Jun. 15, 2004

(54) POINSETTIA 'FISELFI PINK'

(50) Latin Name: *Euphorbia pulcherrima*
Varietal Denomination: Fiselfi Pink

(75) Inventor: Andrea Moes, Koblenz (DE)

(73) Assignee: Florfis AG (CH)

( * ) Notice: Subject to any disclaimer, the term of this patent is extended or adjusted under 35 U.S.C. 154(b) by 46 days.

(21) Appl. No.: 10/382,852

(22) Filed: Mar. 7, 2003

(51) Int. Cl.[7] ..... A01H 5/00
(52) U.S. Cl. ..... Plt./306
(58) Field of Search ..... Plt./306, 303

*Primary Examiner*—Bruce R. Campell
*Assistant Examiner*—June Hwu
(74) *Attorney, Agent, or Firm*—Foley & Lardner

(57) ABSTRACT

A new and distinct Poinsettia plant named 'Fiselfi Pink', characterized as having bright pink colored, pointed bracts; medium sized, star-shaped inflorescence; uniform dark-green foliage with distinct lobes; compact and round, well-branched plant habit; and early flowering response.

1 Drawing Sheet

Latin name of the genus and species of the plant claimed: *Euphorbia pulcherrima.*

Variety denomination: Fiselfi Pink.

BACKGROUND OF THE INVENTION

The present invention relates to a new and distinct cultivar of poinsettia plant known by the variety denomination 'Fiselfi Pink', and botanicallyknown as *Euphorbia pulcherrima.*

'Fiselfi Pink' was derived from a naturally occurring mutation in the variety 'Fiselfi' (U.S. Plant Pat. No. 13,736). 'Fiselfi' is characterized by bright red colored, pointed bracts, dark-green foliage with distinct lobes, and relatively compact plant habit.

The mutation was discovered by Andrea Moes, the inventor, in a greenhouse in Dorsten, Germany, in November, 2000, where among a group of flowering branched plants, a partly pink colored plant was found. The plant was taken to Hillscheid, Germany, and was left to develop vegetative shoots. Cuttings from the mutated branched were used for vegetative propagation in the first act of asexual reproduction, in the spring of 2001. The resulting plants appeared uniform, and the pink bract color was stable. This result was confirmed when the propagation and examination was repeated on a larger scale in the fall of 2002.

Horticultural examination of the clone starting in 2001 and continuing thereafter has demonstrated that the combination of characteristics as herein disclosed for 'Fiselfi Pink' are firmly fixed and retained through successive generations of asexual reproduction.

BRIEF SUMMARY OF THE INVENTION

The following traits have been repeatedly observed and are determined to be basic characteristics of 'Fiselfi Pink', which in combination distinguish this Poinsettia as a new and distinct cultivar:

1. bright pink colored, pointed bracts;
2. medium sized, star-shaped inflorescence;
3. uniform dark-green foliage with distinct lobes;
4. compact and round, well-branched plant habit; and
5. early flowering response.

'Fiselfi Pink' has not been observed under all possible environmental conditions. The phenotype may vary significantly with variations in environment such as temperature, light intensity, and day-length. The following observations, measurements and comparisons describe plants grown in Hillscheid, Germany, under greenhouse conditions which approximate those generally used in commercial practice.

Of the many commercial cultivars known to the inventor, the most similar in comparison to 'Fiselfi Pink' is the parental cultivar 'Fiselfi', and the comparison cultivar 'Fissonosa' (U.S. Plant Pat. No. 10,182).

In contrast to the red colored bracts of 'Fiselfi', 'Fiselfi Pink' has pink colored bracts, a somewhat smaller plant habit, and slightly less distinct expression of lobes of bracts and leaves.

In comparison to 'Fissonosa', 'Fiselfi Pink' has a somewhat deeper and more uniform tone of bract color (a relatively little difference of color between older and younger bracts), and the bract aspect is somewhat upward directed, while the bract aspect of 'Fissonosa' is horizontal or directed slightly downward. Furthermore, the plant habit of 'Fiselfi pink' is more compact, and plants are generally more tolerant to low temperature during cultivation.

BRIEF DESCRIPTION OF THE DRAWINGS

The accompanying color photographic drawing shows typical inflorescence and foliage of 'Fiselfi Pink', with colors being as true as possible with illustrations of this type. The photograph shows a mature potted plant.

DETAILED BOTANICAL DESCRIPTION

The plants describ d were grown in a greenhouse in Hillsch id, Germany, in the fall of 2002. Rooted cuttings were planted into 14 cm pots on Jul. 25, 2002, and were pinched on Aug. 8, 2002, leaving 7–8 leaves. Initially, the temperature was between a minimum of 19° C. and A maximum of 24.5° C. (ventilation temperature), and beginning October 1, a lower temperature, minimum 16° C. to 23° C.

The plants initiated flowers under short-day conditions under natural short-day conditions in the fall, black cloth was not applied. Observations and measurements were mainly taken in mid December, when the plants were in full flower, about 20 weeks old.

In the following description color references are made to The Royal Horticultural Society Colour Chart (R.H.S.). The color values were determined indoors in a north light.

Plant:

*Form.*—Shrub, self-branching.

*Growth habit.*—Compact, well-branched, tight, pinched plants are bushy and round in shaped.

*Height (above soil line).*—18.5 cm.

*Width.*—36–40 cm.

*Average number of branches.*—8.

*Average branch length.*—13–14 cm.

*Branch diameter.*—0.4 cm.

*Average number of inflorescences.*—7.

*Stem color.*—Base color light green, RHS 143 B, to olive, near RHS 146 A, in parts.

*Internode length.*—10–15 mm.

*Rooting.*—Medium, sufficiently rooted for transplanting after about 20–24 days in a greenhouse at a temperature of 22–24° C.

*Blooming habit.*—Begin under natural short day conditions in the fall; botanically (cyathia open) in early December; commercially (bracts colored, marketable): in late November.

*Flowering response time.*—About 8 weeks.

Foliage:

*Leaf arrangement type.*—Alternate.

*Shape.*—Acute base, distinctly lobed with pointed tips, pointed lobes, and acuminate tip (apex), entire margin (apart form the lobes).

*Texture and veination.*—Upper surface: smooth and flat, only weakly veined, lower surface: flat and smooth, except for the slightly protruding midrib and finer side veins in a pinnate pattern.

*Vein coloration.*—Upper side pale green, RHS 145 B; lower side pale light green, RHS 145 C.

*Leaf blade size.*—Length 10.5 cm; width 8.5 cm.

*Petiole.*—Length: 5.5 cm on average, diameter: 2 mm.

*Quantity.*—About 35 leaves per plant.

*Color.*—Generally dark green, uniform. Mature foliage: Upper surface, RHS 139 A; under surface, RHS 139 B. New foliage: Upper side RHS 143 A; under side RHS 137 D.

*Leaf petiole.*—Upper side: brownish-pink, RHS 179 C, to light green, RHS 145 B; lower side: RHS 145 B.

*Aspect.*—Petioles are horizontally directed, the leaf blades are horizontally directed or show slightly downward.

Disease resistance: No special observations made.

Flowering description: Whole inflorescence with surrounding bracts about medium sized, star-shaped, slightly funnel-shaped with the bracts somewhat upward directed.

*Diameter.*—About 20–22 cm.

*Inflorescence height.*—3–4 cm.

*Number of bracts per inflorescence.*—9–11 (size over 2 cm).

*Keeping quality.*—Good quality will be maintained for about 4 weeks at minimum, no dropping of bracts, no fading.

Bracts:

*Shape.*—Basically ovate, with rounded to acute base, weak to moderate lobes, and acuminate tips.

*Size of the largest fully colored bract.*—12.1 cm long, 7.3 cm wide.

*Texture.*—Smooth and flat, with the veins hardly visible, initially no rugosity, as the bracts mature the bracts may appear slightly rippled.

*Vein coloration.*—Upper side corresponds closely to bract color, lower side: dull pink, near RHS 51 B.

*Color.*—Generally bright pink, relatively uniform. Upper surface: Between RHS 52 B and 52 C. Lower surface: Between RHS 52 C and 52 D.

*Petiole.*—22 mm long, upper side color brownish-red, RHS 47 A, lower side145 B, light green.

*Cyme.*—Approximately 20 mm in diameter, about 10 cyathia borne in a tight cluster.

*Cyathium.*—Ovate, 4–5 mm in diameter, medium to light green colored, RHS 143 B, top rose-red, RHS 52 A.

*Peduncle.*—Light green, RHS 144 B, about 2 mm long.

*Nectar cups.*—Usually one per cyathium, about 4 mm wide, golden yellow colored, from RHS 14 A to 17 A, occasionally as orange as RHS 25 A, no reddish infusion near margin.

*Reproductive organs.*—Stamens: About 10–20 in a cluster, filaments short, 2 mm, red colored, RHS 46 B; moderate pollen, yellow, RHS 13 A. Pistil: Style and stigma reddish, RHS 52 A, stigma trifurcate, 6-lobed. Ovaries: Light to medium green, RHS 143 B, initially obovate, later triangular, diameter 4 mm, 6 mm long, 3 ovules.

*Fruit/seed set.*—No seed set observed.

I claim:

1. A new and distinct Poinsettia plant named 'Fiselfi Pink' as illustrated and described herein.

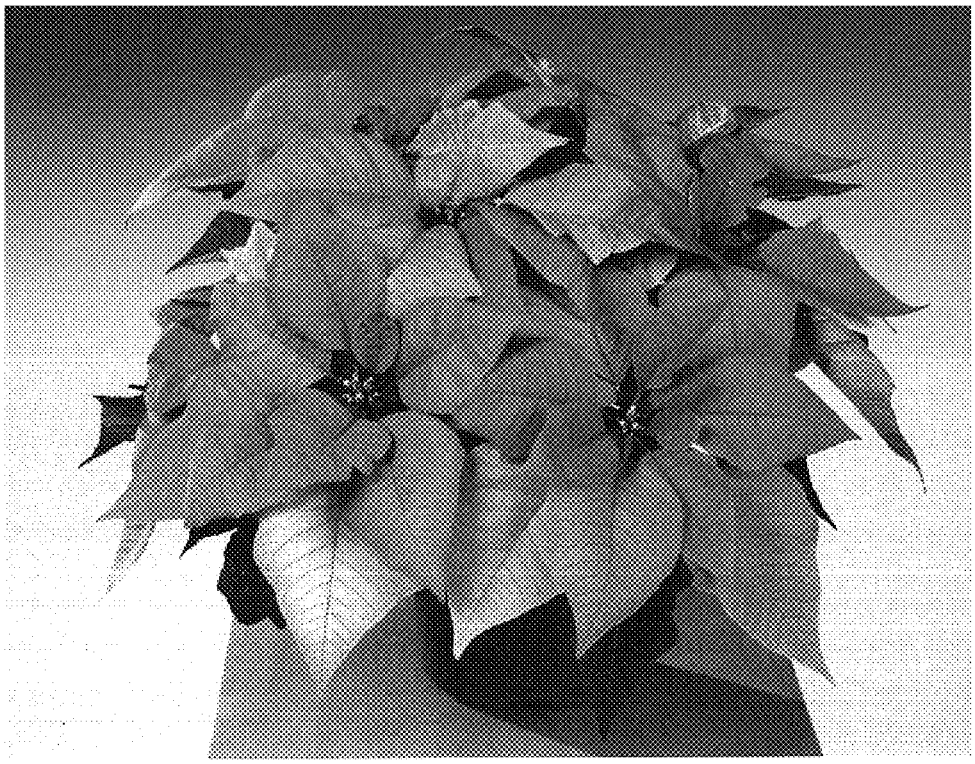

* * * * *